United States Patent [19]
Steadman et al.

[11] Patent Number: 5,928,252
[45] Date of Patent: Jul. 27, 1999

[54] DEVICE AND METHOD FOR DRIVING A NEEDLE AND MENISCAL REPAIR

[75] Inventors: J. Richard Steadman, Vail; Vincent P. Novak, Edwards, both of Colo.

[73] Assignee: ReGen Biologics, Inc., Redwood City, Calif.

[21] Appl. No.: 08/922,911

[22] Filed: Sep. 3, 1997

Related U.S. Application Data

[63] Continuation-in-part of application No. 08/784,562, Jan. 21, 1997.

[51] Int. Cl.⁶ ..................................................... A61B 17/04
[52] U.S. Cl. ........................... 606/148; 606/139; 606/228
[58] Field of Search ................................ 606/1, 108, 139, 606/144, 147, 148, 222, 224, 228

[56] References Cited

U.S. PATENT DOCUMENTS

| | | |
|---|---|---|
| 2,579,192 | 12/1951 | Kohl . |
| 2,610,631 | 9/1952 | Calicchio . |
| 2,738,790 | 3/1956 | Todt, Sr. et al. . |
| 2,808,055 | 10/1957 | Thayer . |
| 4,244,370 | 1/1981 | Furlow et al. . |
| 4,373,976 | 2/1983 | Flanagan et al. . |
| 4,779,616 | 10/1988 | Johnson . |
| 4,781,190 | 11/1988 | Lee . |
| 4,836,205 | 6/1989 | Barrett . |
| 4,926,860 | 5/1990 | Stice et al. . |
| 4,946,462 | 8/1990 | Watanabe . |
| 4,968,317 | 11/1990 | Tormala et al. . |
| 5,059,206 | 10/1991 | Winters . |
| 5,100,415 | 3/1992 | Hayhurst . |
| 5,100,418 | 3/1992 | Yoon et al. . |
| 5,129,912 | 7/1992 | Noda et al. . |
| 5,250,055 | 10/1993 | Moore et al. . |
| 5,281,235 | 1/1994 | Haber et al. . |
| 5,304,184 | 4/1994 | Hathaway et al. . |
| 5,320,633 | 6/1994 | Allen et al. . |

(List continued on next page.)

OTHER PUBLICATIONS

Cannon, W. D., Jr., "Arthroscopic Meniscal Repair" Operative Arthroscopy, ed. J.B. McGinty et al., Raven Press, New York, 1991.

Horibe et al., "Results of Isolated Meniscal Repair Evaluated by Second–Look Arthroscopy" Arthroscopy: The Journal of Arthroscopic and Related Surgery 12:150–155, 1996.

"The Zone Specific II Meniscal Repair System", Linvatec Brochure, 1994.

Meniscus Arrow Brochure, Bionix, Inc.

"The Concept Spectrum Tissue Repair System Surgical Technique for All–Inside Meniscus Repair", Linvatec Brochure, 1992.

"Endoscopic Meniscal Repair Using the T–FIX", Acufex Microsurgical, Inc. Brochure, 1994.

"Everything You Need for Complete Meniscal Repair", Acufex Microsurgical, Inc. Brochures, 1988.

Clancy et al., "Arthroscopic Meniscal Repair," Univ. of Wisconsin, Dept. of Surgery, Div. of Orthopedic Surgery, Madison, Wisconsin.

*Primary Examiner*—Glenn K. Dawson
*Attorney, Agent, or Firm*—Fish & Richardson P.C.

[57] ABSTRACT

A driver assembly including a handle configured to receive a detachable cannula, a trigger arm connected to the handle, and an advancement mechanism mechanically coupled to the trigger arm. The advancement mechanism is constructed to receive and incrementally translate the surgical device through the cannula into body tissue to be repaired in response to a force applied to the trigger arm. The driver assembly of the present invention is useful whenever it is desired to incrementally advance a surgical device such as a long needle or obturator into tissue. The incremental advancement feature of the driver assembly enables an operator to control the precise placement of the surgical device. The driver assembly is particularly useful in applications where advancing the needle or obturator is difficult due to space restriction or when an easily operable surgical device is required.

20 Claims, 13 Drawing Sheets

U.S. PATENT DOCUMENTS

| | | |
|---|---|---|
| 5,364,410 | 11/1994 | Failla et al. . |
| 5,387,227 | 2/1995 | Grice . |
| 5,391,174 | 2/1995 | Weston . |
| 5,405,354 | 4/1995 | Sarrett . |
| 5,431,666 | 7/1995 | Sauer et al. . |
| 5,433,722 | 7/1995 | Sharpe et al. . |
| 5,439,467 | 8/1995 | Benderev et al. . |
| 5,447,512 | 9/1995 | Wilson et al. . |
| 5,454,821 | 10/1995 | Harm et al. . |
| 5,467,786 | 11/1995 | Allen et al. . |
| 5,486,186 | 1/1996 | Yoon . |
| 5,489,288 | 2/1996 | Buelna . |
| 5,501,692 | 3/1996 | Riza . |
| 5,507,754 | 4/1996 | Green et al. . |
| 5,531,699 | 7/1996 | Tomba et al. . |
| 5,624,431 | 4/1997 | Gerry et al. ............................... 606/1 |
| 5,643,319 | 7/1997 | Green et al. . |

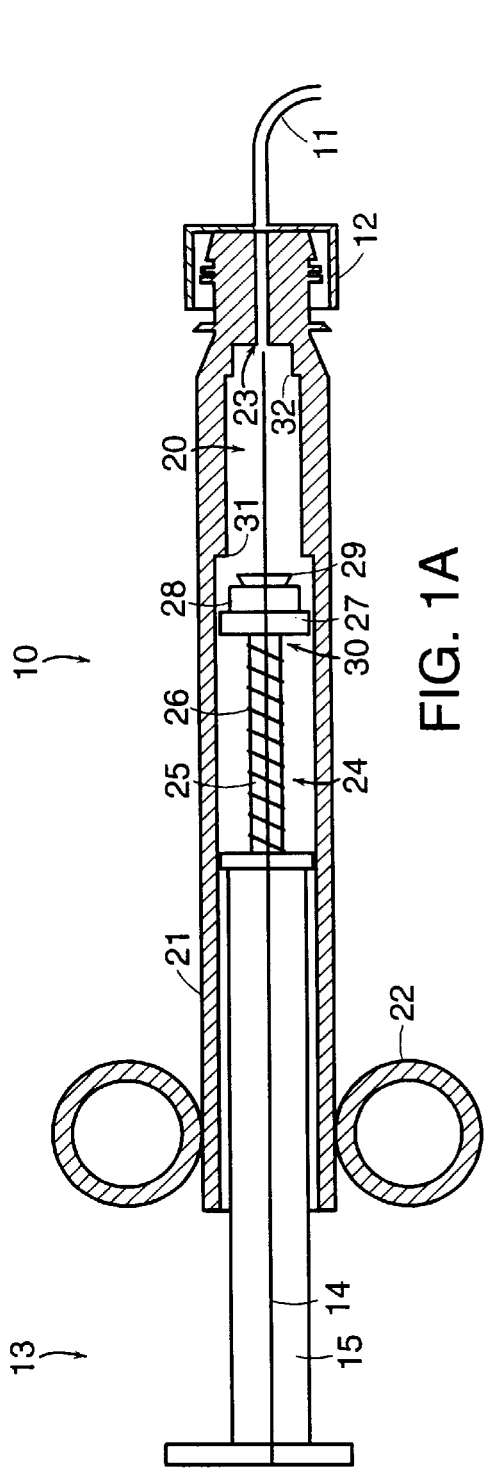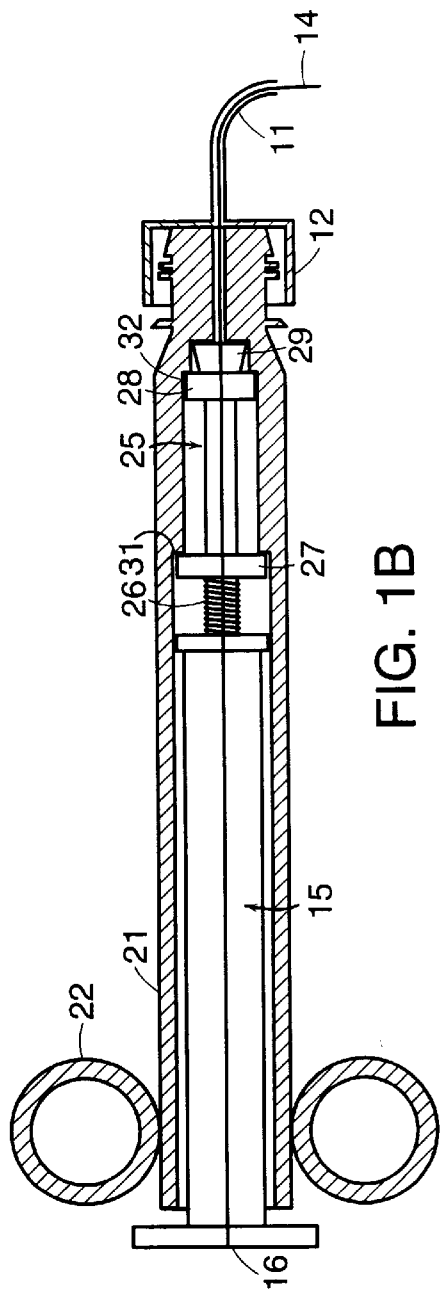

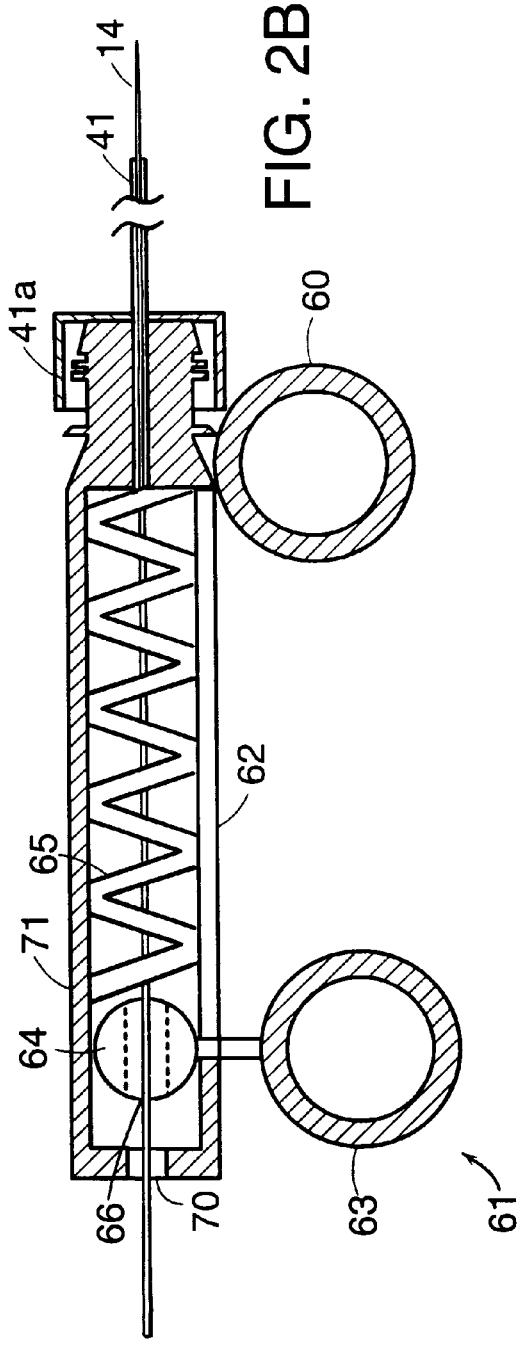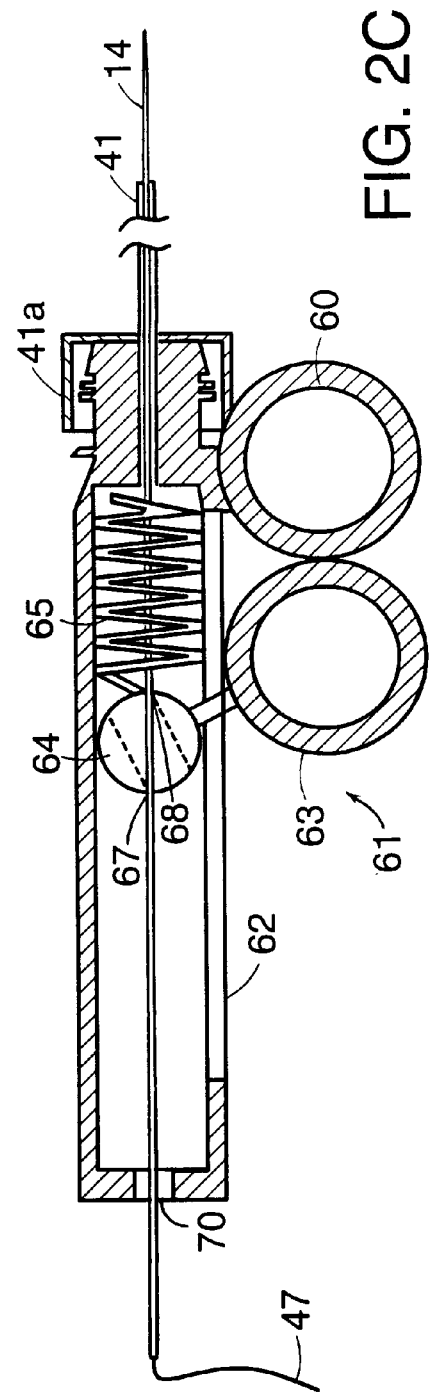

DEVICE AND METHOD FOR DRIVING A NEEDLE AND MENISCAL REPAIR

This application is a continuation-in-part of application Ser. No. 08/784,562, filed Jan. 21, 1997.

FIELD OF THE INVENTION

The present invention relates generally to a device and method for incrementally advancing surgical devices, such as needles and tissue anchors. More particularly, the present invention relates to devices and methods for incrementally advancing such surgical devices to repair tears in the meniscus of the knee.

BACKGROUND OF THE INVENTION

Injury to the knee involving a tear in the meniscus is a common occurrence, often in the context of athletic events, and is prevalent in the younger population. The meniscus is recognized as being vital to the biomechanical stability and protection of the knee joint. Damage to the meniscus can greatly increase the likelihood of the articular surfaces of the knee joint developing conditions such as osteoarthritis. A common remedy in the past for tears in the meniscus involved removal of the meniscus. However, this is not a favored option as it has been shown that degenerative changes in the knee are directly proportional to the amount of meniscus removed. Thus, in many instances it is desirable to repair the torn meniscus with the objective being to prevent instability of the knee joint and to prevent onset of conditions such as osteoarthritis.

Current methods for repairing tears in the meniscus are technically very challenging for the surgeon. One widely used technique requires that a long needle with a suture be passed through the torn meniscus and the knee joint. The needle carrying the suture is passed through the meniscus and the knee in its entirety several times until the meniscal tear is closed. As this procedure is typically performed arthroscopically, the amount of space available within the knee for manipulating the long needle through the meniscus is extremely limited. The procedure often requires more than one pair of hands, with one pair inserting the needle into the knee while another pair uses graspers, operating in the limited inflated space in the interior of the knee, to shuttle the needle through the meniscus and out the other side of the knee.

Using such current methods, it is difficult for a surgeon to advance the entire needle without the use of a number of other instruments, which complicates the procedure and may unnecessarily damage tissue in the operating area. Furthermore, it is difficult to manipulate and advance a long thin needle for penetrating the meniscus and the surrounding tissue in the knee without an aptly designed driving mechanism. The needle typically needs to penetrate the skin on the anterior side of the knee, pass through the synovial sac and the torn meniscus, and exit on the posterior side of the knee. Having a needle driver would reduce the complexity of manipulating and passing the needle through the knee.

An alternative meniscal repair technique involves the implantation of resorbable anchors into the meniscus in order to fasten torn or displaced tissue. Systems for delivering meniscal anchors are commercially available from Bionix, Inc., Malvern, Penn., under the trade name Meniscus Arrow™. The arrows are formed from a resorbable material (polylactic acid) and are elongate elements having barbs spaced-apart along their lengths. The anchors are delivered through a canula by insertion using a blunt obturator.

Both suturing and the use of anchors will continue to find use in performing meniscal repairs. Often times, however, it is not known at the outset of a repair procedure whether the use of sutures or anchors would be most beneficial. Thus, it may become necessary to use two entirely different repair systems during the course of a single arthroscopic meniscal repair procedure. Such duplication is both costly and inconvenient. In some cases, the treating physician may decide to use only a single system even though use of both types of repairs would be most beneficial to the patient.

For these reasons, it would be desirable to provide improved devices and methods for repairing tears in the soft tissue of the body. It would be particularly desirable to have devices and methods for incrementally advancing a needle into the body for suturing meniscal tears in the knee. It would be further desirable to provide devices and methods which are able to perform both suturing and the delivery of meniscal anchors with only minor modifications.

SUMMARY OF THE INVENTION

The present invention provides a driver device for incrementally advancing a surgical device, such as a long needle or obturator, which are commonly required in certain surgical techniques including those used to repair meniscal tears in the knee.

In a general aspect of the invention, the driver assembly includes a handle configured to receive a detachable cannula, a trigger arm connected to the handle, and an advancement mechanism mechanically coupled to the trigger arm. The advancement mechanism is constructed to receive and incrementally translate the surgical device through the cannula and into the body tissue to be repaired in response to a force applied to the trigger arm.

Among other advantages, the driver assembly of the present invention is useful whenever it is desired to incrementally advance a surgical device such as a long needle or obturator into tissue. The incremental advancement feature of the driver assembly enables an operator to control the precise placement of the surgical device. The driver assembly is particularly useful in applications where advancing the needle or obturator is difficult due to space restriction or when an easily operable surgical equipment is required. Furthermore, the driver assembly is able to produce countering forces on the surgical device when desired. For example, the driver assembly is capable of providing a force greater than that which is provided by the operator such that one gentle squeeze of the trigger arm translates into a forceful push of the needle. This enables the operator to penetrate hard tissue or cartilage with the needle with ease. Alternatively, the driver assembly is able to produce a force less than that provided by the operator. In this case, one squeeze of the trigger arm produces a gentle push of the needle thereby enabling the operator to perform delicate puncturing of soft tissue with significantly reduced chance of error which minimizes patient trauma.

Embodiments of this aspect of the invention may include one or more of the following features.

The advancement mechanism includes a shuttle reciprocatably mounted to the handle, and a cam member pivotally connected to the shuttle. The cam member is configured to clamp the surgical device against the shuttle in response to the force applied to the trigger arm during the incremental advancement of the surgical device. The driver assembly also includes a return mechanism configured to urge the shuttle towards a proximal end of the handle when the force applied to the trigger arm is released so that the shuttle is in position to once again advance the surgical device. In certain embodiments, the return mechanism includes a spring positioned between the shuttle and a distal end of the handle to urge the shuttle towards the proximal end of the handle in response to release of the force applied to the trigger arm.

In some embodiments, the driver assembly further include a force-converter device connected to the trigger arm and to the advancement mechanism. The force-converter device is constructed to cause rotation of the cam and subsequent incremental lineal motion of the shuttle towards the distal end of the handle in response to the force applied to the trigger arm. The force-converter device includes a spring connected between the trigger arm and the handle. Additionally, the force-converter device includes lever arms connected between the trigger arm and the advancement mechanism to translate motion of the trigger into motion of the advancement mechanism.

The driver assembly further includes a cannula removably connected to the distal end of the handle. The cannula has a length sufficient to extend from the surface of the skin to the surgical sight of the body tissue being repaired. The handle also includes an annular tube axially aligned with the cannula. The tube has a funnel-shaped opening at a proximal end to guide and direct the surgical device into the tube, the cannula being removably connected to a distal end of the annular tube.

In another aspect of the invention, the above described driver assembly is used to repair a body tissue tear. The method includes inserting a surgical device in the advancement mechanism, and positioning the cannula of the driver assembly through a skin opening at a target site adjacent the tissue tear. The advancement mechanism is actuated by forcing the trigger arm towards the handle, thereby incrementally advancing the surgical device through the cannula and the body tissue tear until at least a portion of the surgical device passes through a posterior surface of the body tissue.

Embodiments of this aspect of the invention may include one or more of the following features.

The surgical device is of a type having a length of suture connected to it such as a suture needle. In this embodiment, the surgical device is removed from the body, and the length of suture is disconnected from the surgical device. In some cases, another surgical device, having the length of suture connected to it, is inserted in the advancement mechanism, and the cannula is positioned through a skin opening at another target site adjacent the tissue tear. The advancement mechanism is then actuated by forcing the trigger arm towards the handle, thereby incrementally advancing the second surgical device through the cannula and the body tissue tear until at least a portion of the second surgical device passes through the posterior surface of the body tissue. The second surgical device is removed from the body. The length of suture is disconnected from the second surgical device, and the suture is tied. The surgical device may be an implant. The implant may be made of biocompatible, bioresorbable material which may be collagen or plastic. The surgical device may also be an obturator (e.g., a resorbable meniscal arrow) which is implanted into the meniscus to fasten torn tissue.

BRIEF DESCRIPTION OF THE DRAWING

FIG. 1A is a cross-sectional view of a plunger-type needle driver device loaded with a long needle and having a J-shaped cannula at a distal end of the device.

FIG. 1B is a cross-sectional view of the device in FIG. 1A with the plunger displaced towards the distal end of the device.

FIG. 2B is a cross-sectional view of a torsional ratchet needle driver device loaded with a long needle carrying a suture and having a straight cannula at a distal end of the device.

FIG. 2C is a cross-sectional view of the device in FIG. 2B with the torsional ratchet gripping the long needle and displaced towards the distal end of the device.

DESCRIPTION OF THE PREFERRED EMBODIMENTS

Figure 2A:
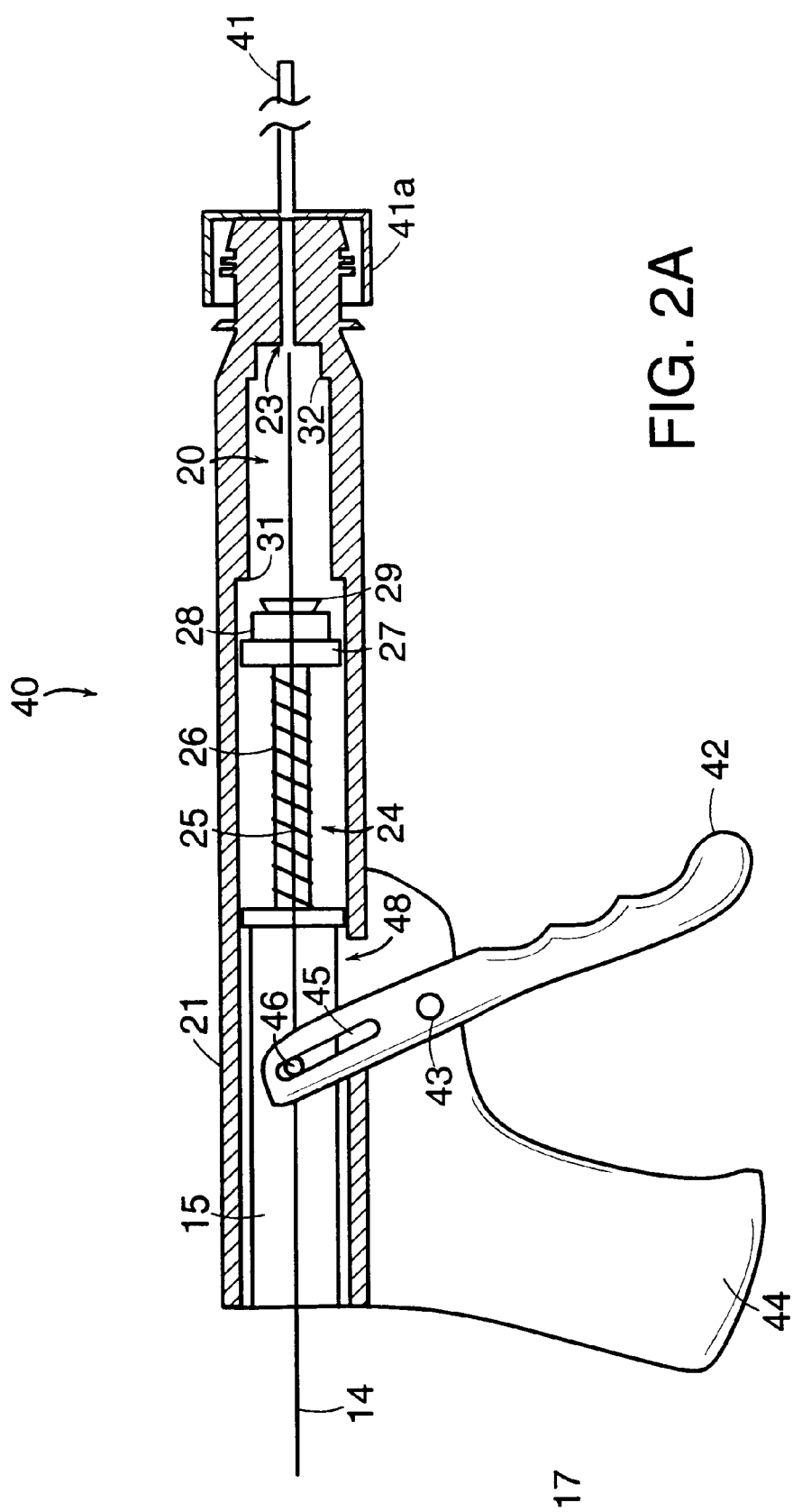
FIG. 2A is a cross-sectional view of a pistol grip needle driver device loaded with a long needle carrying a suture and having a straight cannula at a distal end of the device.

The present invention provides devices and methods for driving elongate elements, such as long needles and tissue anchors, into the body as would be required in certain procedures for repairing the soft tissue therein. The invention particularly is useful for meniscal repair procedures where meniscal repairs can be performed by suturing and/or by implanting resorbable anchors. Such devices and methods are described in U.S. Ser. No. 08/784,562, filed Jan. 21, 1997, the entire contents of which are hereby incorporated by reference.

Referring now to FIG. 1A and 1B, an exemplary embodiment of a driver 10 for repairing meniscal tears in the knee will be described. Device 10 is specifically adapted for driving a long needle 14, but will be appreciated that the device may be readily adapted for use in other parts of the body and for delivering different types of anchoring elements, as will be described in more detail below.

FIG. 1A shows a needle driving device 10 using a J-shaped cannula 11 which is removably connected to the device 10 by a luer lock 12. The cannula 11, used in conjunction with a needle driving mechanism 13, functions as a sheath to guide a long needle 14 to its target site. Although this embodiment of the present invention uses a J-shaped cannula 11 formed for providing better access to the damaged tissue, the cannula 11 can be of various shapes and made from various materials, so long as the resulting structure has a sufficient length and strength to guide the needle 14 to the target site without the needle 14 or cannula 11 damaging other tissue on their way to the site. Further, the cannula 11 needs to provide a good access angle so that the needle enters the meniscus and exits the knee at the desired locations. Typically, the cannula 11 ranges in length from 6 cm to 10 cm. It has an outer diameter ranging from 0.5 to 5 millimeters and a lumen diameter ranging from 0.25 to 4.5 millimeters (not illustrated).

The driving mechanism 13 functions to advance a long needle 14 through cannula 11. Suitable driving mechanisms will be able to grip the needle 14 securely to push the needle 14 through the body tissue as it exits the cannula 11 and also to pass nearly the entire needle into the cannula 11. The needle driving device 10 illustrated in FIGS. 1A and 1B uses a plunger-type needle driving mechanism 13. It should be noted that the needle driving mechanism 13 could have a variety of other constructions. For example, the mechanism 13 could comprise a scissors grip device as illustrated in FIG. 2 and described below. Alternatively, it could be a drive wheel attached to a rack and pinion system that could reciprocate to provide a ratchet-like motion. A rotary system such as a drive wheel powered manually or by an electric motor could frictionally engage the needle to advance the needle through the housing. In further alternate forms, the engagement surface, instead of a collet, could be a pincher which engages and disengages by manual operation. The pincher would engage and disengage according to the amount of pressure applied to it by the operator.

As shown in FIGS. 1A and 1B, the needle driving mechanism 13 comprises a shuttle 15 having a central bore 16 that allows the long needle 14 to be slidably engaged within the shuttle 15. The shuttle 15 translates axially inside a lumen 20 of a housing 21 in a reciprocating manner. By using the fingers to grip rings 22, the shuttle 15 can be pushed towards the distal end 23 of lumen 20 by depressing the shuttle 15 with the thumb.

The housing 21 in which the shuttle 15 and collet mechanism 24 (described below) slides, does not need to entirely cover the shuttle or the collet. The purpose of the housing 21 is to provide a track on or in which the shuttle 15 and collet mechanism 24 may reciprocate and to provide mount points for the stops which actuate the collet to release the needle engaged by it. For instance it would not be necessary to have a completely enclosed housing. It could be any type of open or closed frame such as a series of rings mounted onto an axial support piece (not illustrated). The rings would contain the shuttle and collet to prevent them from disengaging.

As shown in FIG. 1A, the needle driving mechanism 13 is connected to a collet mechanism 24. The collet mechanism 24 functions to engage and disengage the needle as the driving mechanism 13 moves in a reciprocating manner inside the housing 21. This function can be fulfilled by the device described herein or by other mechanisms that engage and disengage the needle as the shuttle translates towards the distal end of the housing. Alternate embodiments of the invention could mate different needle driving mechanisms to different collet mechanisms. In the present embodiment, the collet mechanism 24 comprises an extended member 25, a compression spring 26, a stop 27, a collet sleeve 28, and a collet 29. The extended member 25 has a central bore (not illustrated) that aligns axially with the central bore 16 in shuttle 15. The compression spring 26 is concentrically mounted about the extended member 25 and the spring urges apart shuttle 15 and stop 27. The stop 27 is mounted slidably and concentrically about the extended member 25. When the shuttle 15 is proximally retracted, the stop 27 presses against a distal end 30 of the compressing spring 26 while the collet sleeve 28 is in contact with both the stop 27 and the collet 29.

Referring now to FIG. 1B, as the shuttle 15 advances towards the distal end 23 of the lumen 20 in the housing 21, the stop 27 is picked off by lip 31 in the housing 21. The extended member 25 continues to pass through the stop 27 until the collet 29 touches the distal end 23 of the lumen 20. As the collet mechanism 24 nears the distal end 23 of the lumen 20 but before contacting the distal end 23, the collet sleeve 28 is picked off by distal lip 32. When the collet sleeve 28 is picked off, this releases contact between the collet 29 and the long needle 14. This allows the needle 14 to be advanced and then released so that the needle 14 can be re-engaged by the collet 29 at a point where the advancement of the needle 14 can be preserved when the shuttle 15 and collet mechanism 24 are retracted. The shuttle 15 and collet mechanism 24 are actuated multiple times in this manner to advance the long needle 14 through the needle driving device 10.

When the collet 29 is depressed and held at the distal end 23 of the lumen 20, the collet 29 is no longer frictionally engaged with the needle 14. The needle 14 is free to be slidably inserted or removed from the needle driver 10. This quality allows for manipulation of the needle 14 without adjusting the shuttle 15 or actuating the needle driving mechanism 13. This may facilitate removal or insertion of the needle 14 into the needle driving device 10.

FIG. 2A shows an alternate embodiment of the device of the present invention comprising a scissors grip needle driver device 40 with a straight cannula 41 and a luer connector 41a. The device 40 is loaded with a long needle 14 carrying a suture 47. A lever arm 42 is connected to the shuttle 15 for translating the shuttle axially in the housing 21. The lever arm 42 pivots about pivot 43 which is mounted onto a pistol grip 44. The lever arm 42 has a slot 45 which engages protrusion 46 on the shuttle 15. The engagement between the slot 45 and the protrusion 46 allows force to be applied to the shuttle 15 when the lever arm 42 is actuated. The lever arm 42 passes into the housing 21 through an entry slot 48 located along the surface of the housing 21. The collet mechanism 24 which is connected to the shuttle 15, operates in the same manner to advance the long needle 14 as the collet mechanism 24 described in FIGS. 1A and 1B. The scissor grip device 40 offers the benefit of mechanical advantage when advancing the needle.

FIGS. 2B and 2C show a further embodiment of the device of the present invention comprising a torsional ratchet needle driver device fitted with a straight cannula. In FIG. 2B, the housing 21 has a grip ring 60 attached at a distal end 61 of the housing. A portion of a torsional ratchet assembly 61 fits slidably through a longitudinal slot 62 into the housing 21. The assembly 61 comprises a ring 63 which remains outside the housing 21 while a torsional gripper 64 is inserted inside the housing 21 for releasably engaging a needle 14. A compression spring 65 urges the assembly 61 to a resting position near the proximal end of housing 21. The ring 63 can translate the assembly 61 along the length of the longitudinal slot 63 and can pivot the assembly to engage the torsional gripper 64 to the needle 14. The torsional gripper 64 contains a passageway 66 having a circumference larger than that of the needle 14. When the assembly 61 is not pivoted and passageway 66 is in longitudinal alignment with needle 14, the needle can be slidably inserted or removed from the housing 21. When assembly 61 is pivoted, as shown in FIG. 2C, the torsional gripper 64 engages needle 14 by torquing edges 67 and 68 of passageway 66 against the needle's shaft. With the needle 14 engaged by the gripper 64, the assembly 61 can translate to advance needle 14 from needle entry port 70 through the housing 21 towards cannula 41. After needle 14 has been advanced, the assembly 61 is unpivoted to disengage the needle, and the assembly is returned by spring 65 to its resting position near the proximal end of the housing. By repeatedly pivoting, translating, and unpivoting the torsional gripper 64, the assembly 61 engages and disengages the needle 14 to create a ratcheting motion necessary to advance a long needle through the present device.

Referring now to FIGS. 3–9, an exemplary method of suturing a meniscal tear T in the knee K will be described in detail. Again, the method as described can be adapted for suturing and other tasks requiring advancing a needle in other parts of the body. This procedure is performed arthroscopically, with the knee inflated with liquid to provide operating space inside the knee. An arthroscope and other instruments typically used in such a procedure have been omitted from the drawings.

Figure 3:
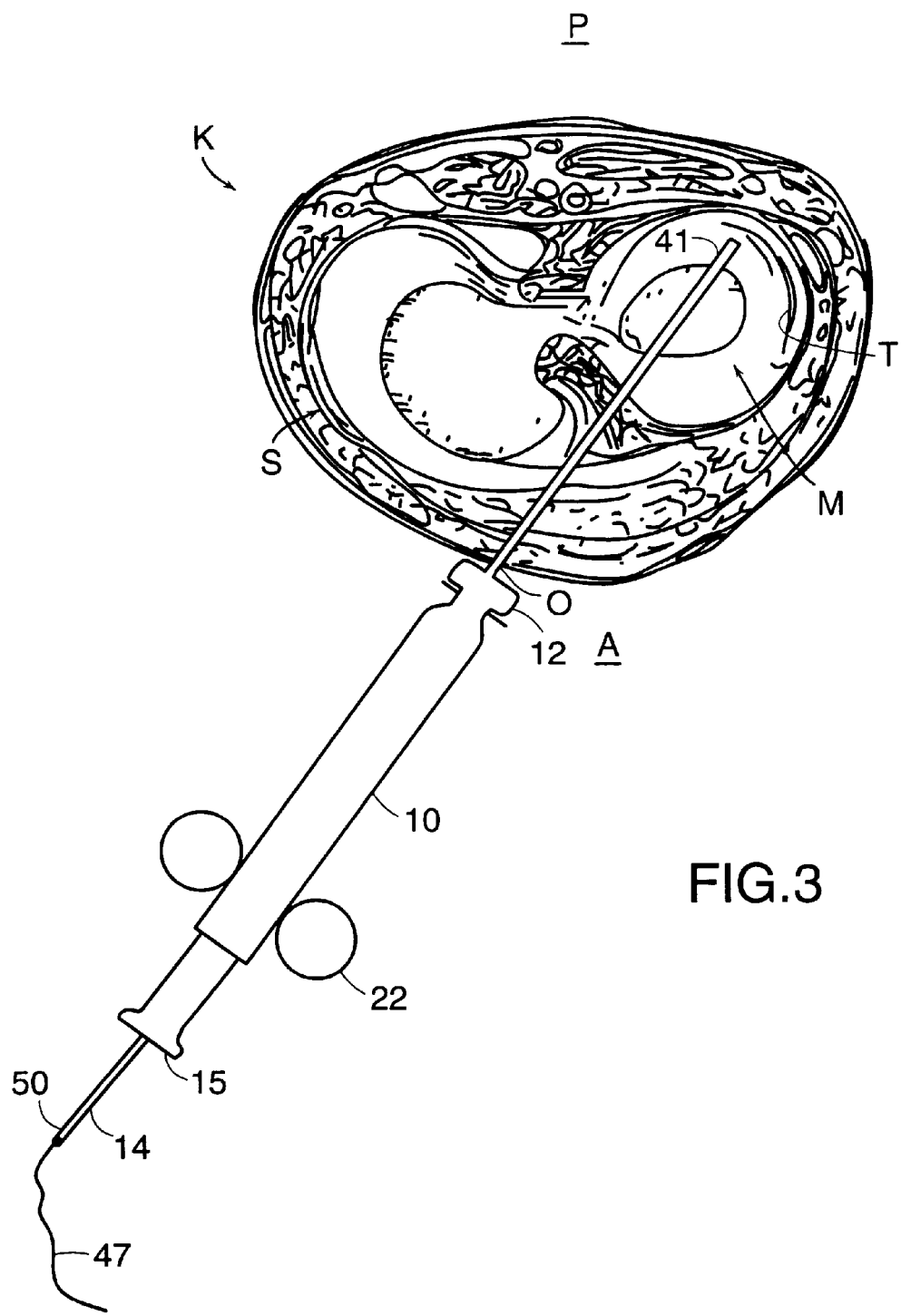
FIG. 3 is the device of FIG. 1A and 1B in a cross-sectional view of a human knee joint having a peripheral tear of the lateral meniscus, as seen from above, with a straight cannula of the device entering from the anterior side of the knee and positioned near the meniscal tear.

FIG. 3 shows the needle driver device 10 with a straight cannula 41 positioned near the site of a peripheral tear T in the lateral meniscus M. It will be appreciated, of course, that the cannula may have a wide variety of shapes and configurations in order to permit access to different portions of the meniscus. Frequently, the cannula will have a J-shaped configuration, as described earlier in connection with FIGS. 1A and 1B. As a further alternative, the cannulas may be malleable or otherwise shapable in order to permit the treating physician to customize the shape for a particular application. The needle driver 10 has entered the knee and the synovial sac S through a percutaneous opening O on the anterior side A of the knee. A long straight needle 14 carrying a suture 47 has been loaded into the needle driving device 10. The needle 14 used with the present invention may be made of a highly flexible material which will enable the needle to pass through variously curved cannulas attached to the needle driving device 10. Preferably, the needle 14 will be formed from stainless spring steel or a superelastic material, such as nickel titanium alloy. Preferred superelastic nickel titanium alloys are available commercially from suppliers, such as Shape Memory Applications, Sunnyvale, Calif., Innovative Technologies International, Beltsville, Md. and Fort Wayne Metals, Fort Wayne, Ind. When used for meniscal repair, the needle 14 will typically be from about 5 cm to 40 cm in length and have a diameter from 0.5 mm to 1.5 mm, usually being about 0.7 mm (0.028 in.). For other purposes, the needle length could vary from 5 cm to 50 cm or longer. The needle 14 will be attached to a suture 47 typically having a length in the range from 45 cm to 150 cm, usually 60 cm to 90 cm. The suture 47 will usually be attached at the proximal end 50 of the needle, but could also be attached at the distal end or anywhere in between. The suture 47 itself will usually be attached near one end thereof, but the point of attachment is not critical so long as sufficient suture length is available to perform the desired procedure. Particular methods for forming needles and attaching needles to sutures are well known in the art.

Figure 4:
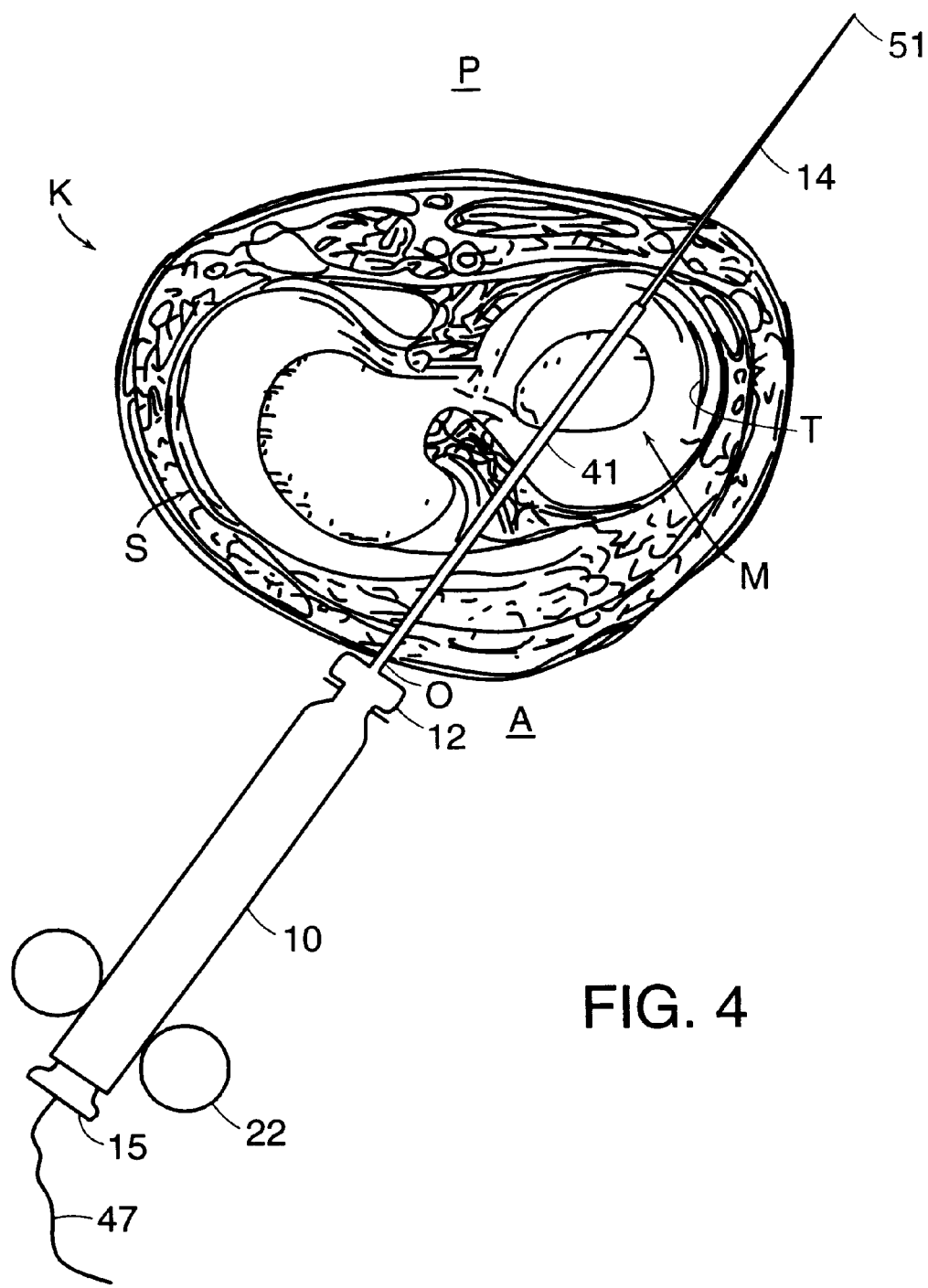
FIG. 4 is the view as in FIG. 3 with the long needle carrying the suture penetrating the meniscus and exiting the posterior side of the knee.

With the cannula 41 near the meniscal tear T, the surgeon begins ratcheting the shuttle 15 to advance the long needle towards a target site of the meniscus adjacent the tear. Under arthroscopic control using either direct vision or television monitor control, the needle is advanced until the distal end 51 of the needle has cleared the cannula 41 and nears the first target site on the meniscus M. Certain that the needle 14 is on target, the surgeon continues reciprocating the shuttle 15 and advances the needle through the meniscus M. As shown in FIG. 4, the surgeon continues advancing the needle 14 until at least the distal end 51 of the needle exits the patient's body on the posterior side P of the knee.

Figure 5:
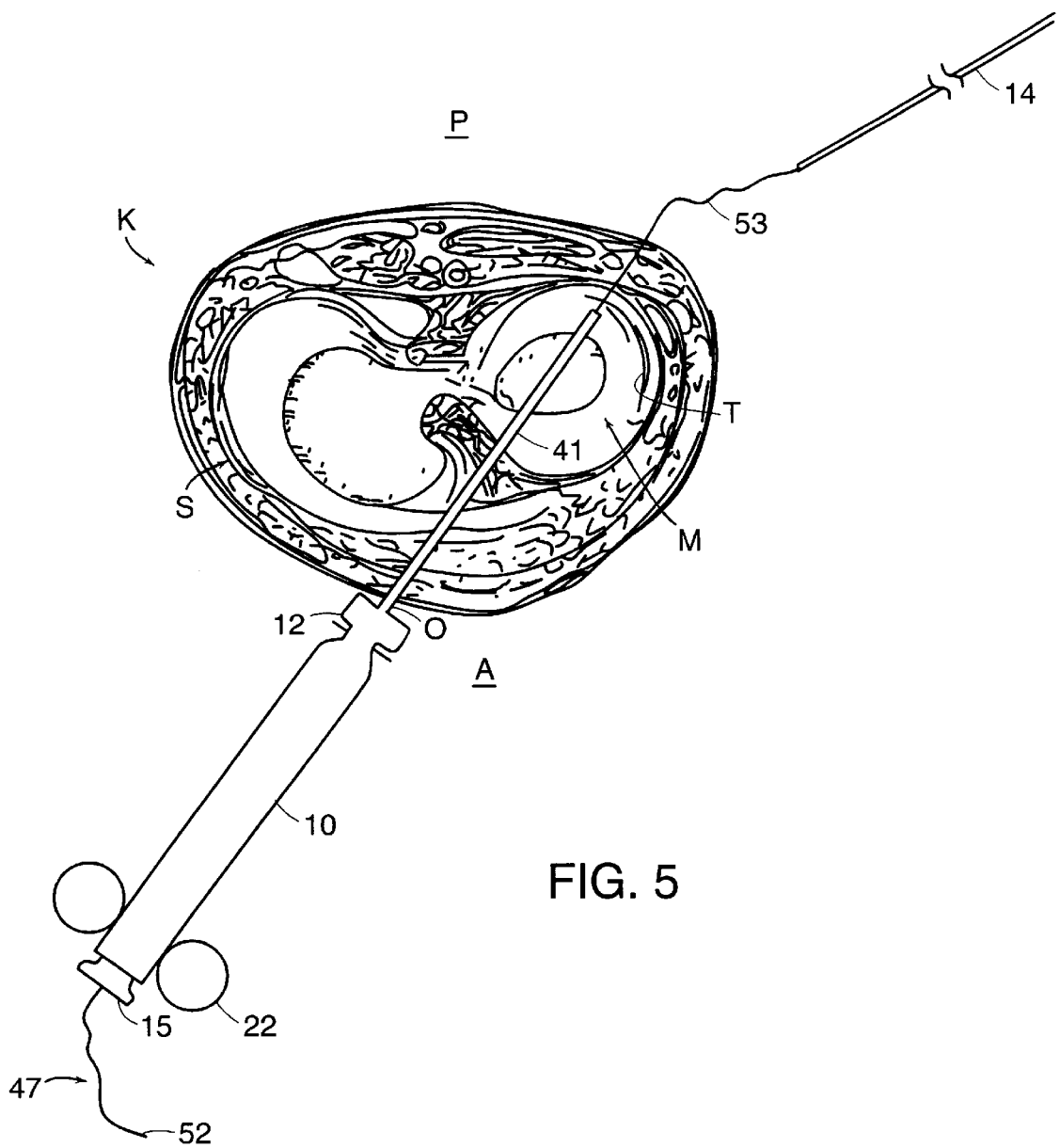
FIG. 5 is the view as in FIG. 3 with the long needle on the posterior side, completely removed from the knee and with the suture detached from it.

In FIG. 5, the needle 14 is completely removed from the knee, and the suture 47 is disconnected from the needle. At this point, one end 52 of the suture 47 is exposed on the anterior side A of the knee while another end 53 is exposed on the posterior side P. The surgeon may attach the same needle 14 or a different one to the length of suture 47 still exposed on the anterior side of the knee. The end 52 of the suture does not need to be attached to the needle 14; any portion of the suture 47 that remains exposed on the anterior side A of the knee will suffice. Further, the suture 47 does not need to attach to the proximal end 50 of the needle. The attachment point on the needle 14 may be at the distal end 51 or somewhere between the distal and proximal ends. The needle 14 is then passed through the knee a second time starting from the anterior side A and passing through a second target site on the meniscus M, using essentially the same method used in the first pass.

Figure 6:
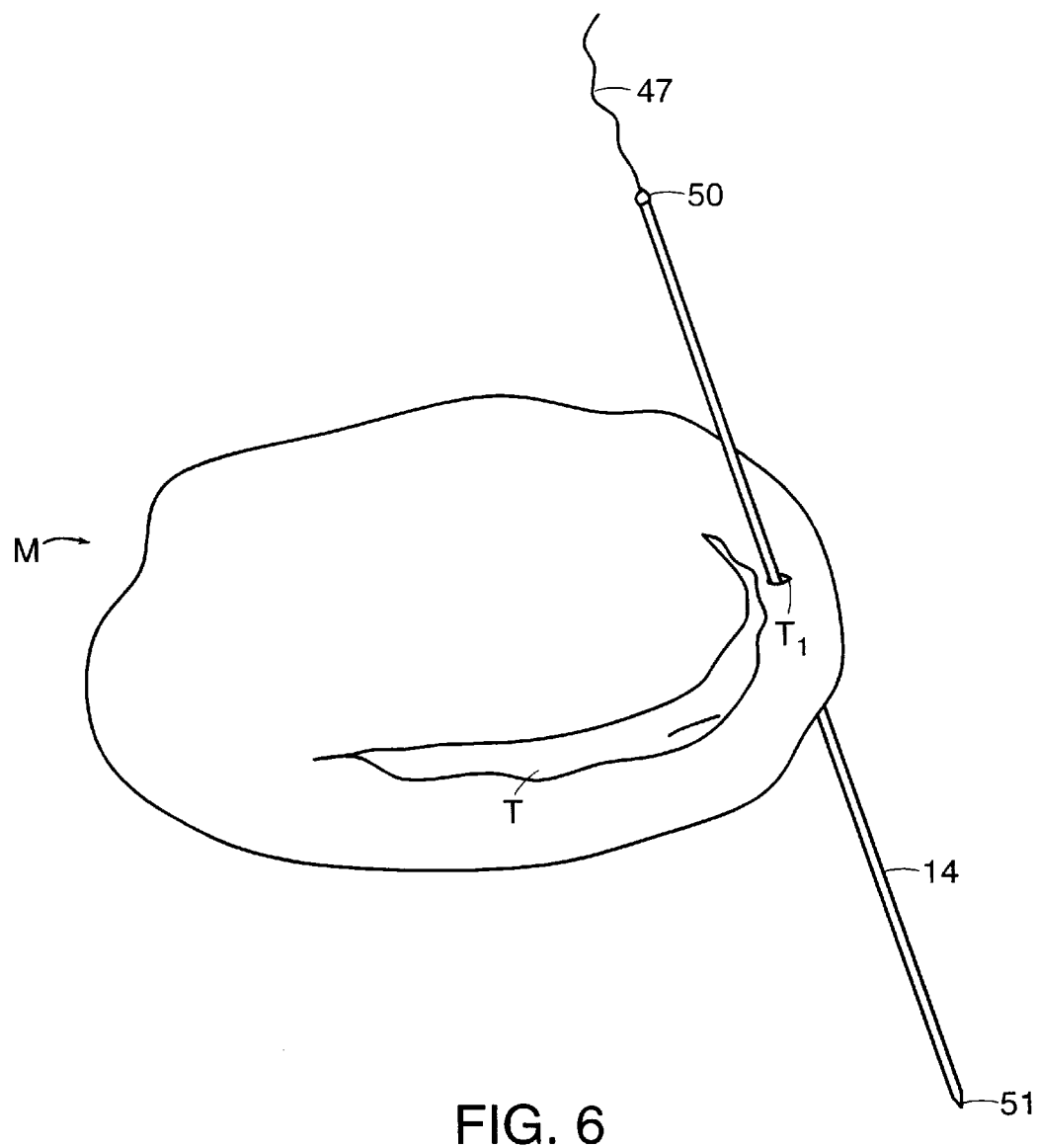
FIG. 6 is an perspective view of the meniscus having a peripheral tear being penetrated by the first pass of the long needle, with the cannula and surrounding tissue omitted.
Figure 7:
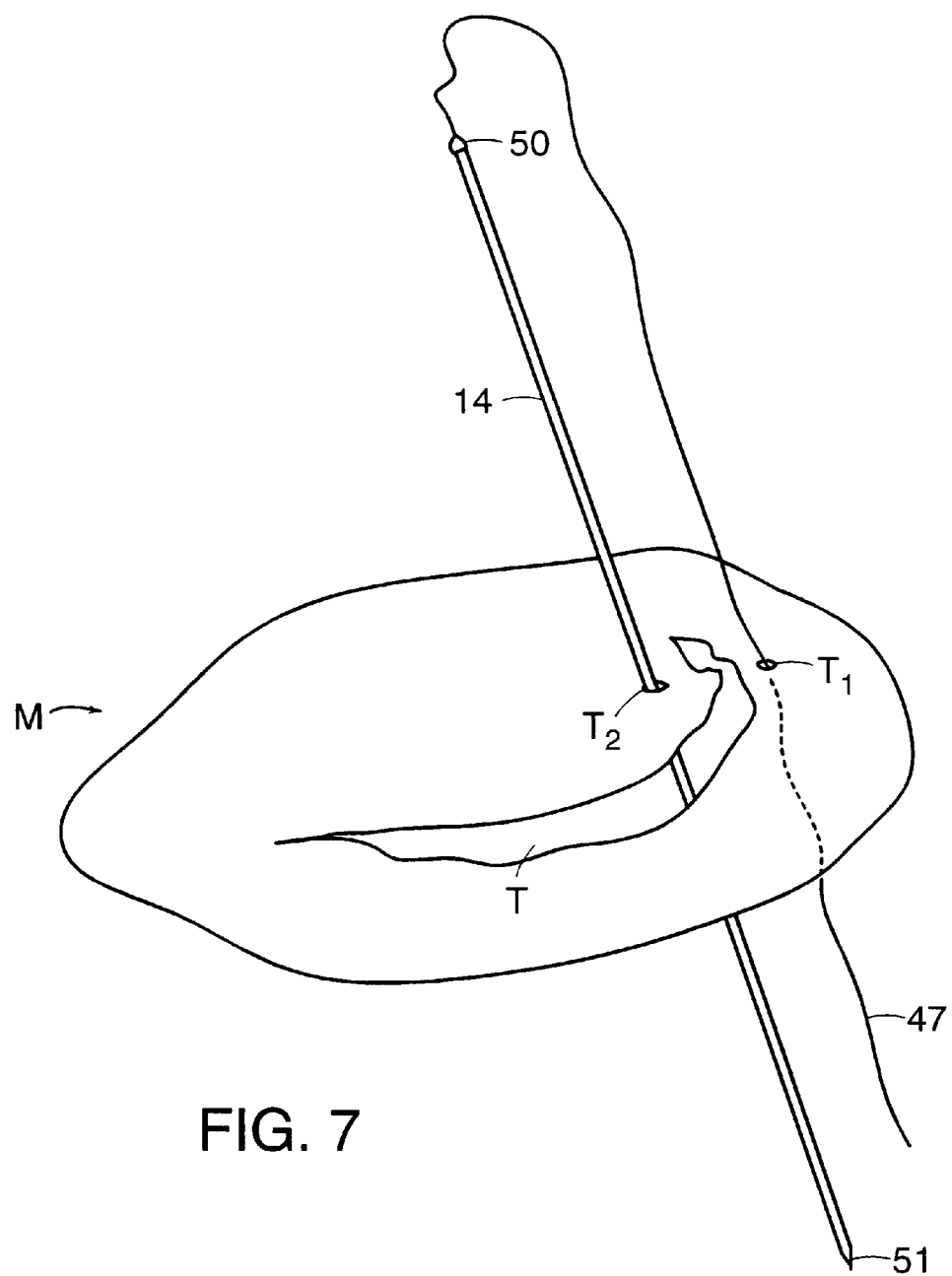
FIG. 7 is the view in FIG. 6 with the needle making a second pass through the meniscus.
Figure 8:
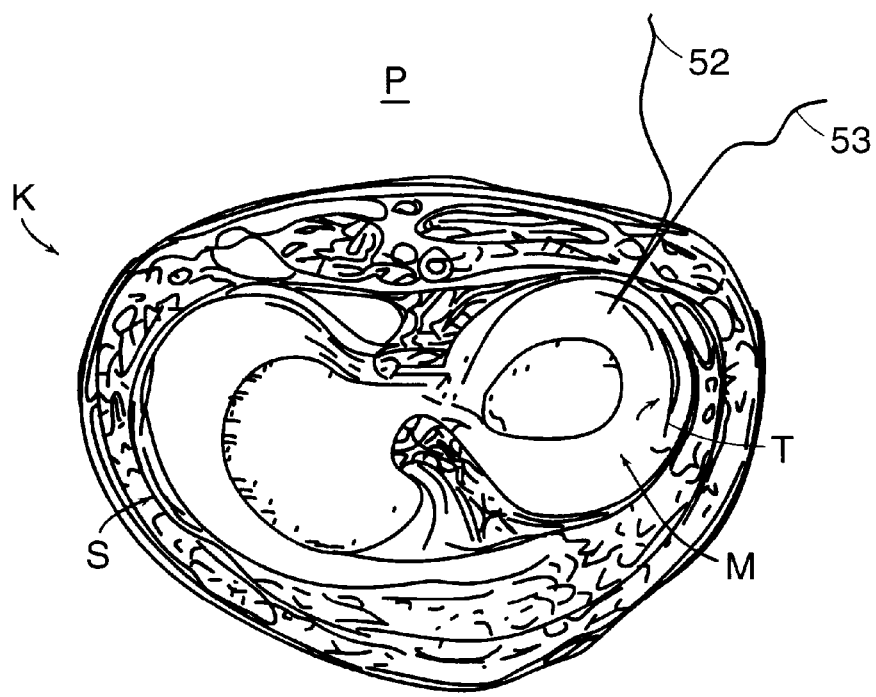
FIG. 8 is cross-sectional view of the knee as view from above showing both ends of the suture lying outside the posterior side of the knee.
Figure 9:
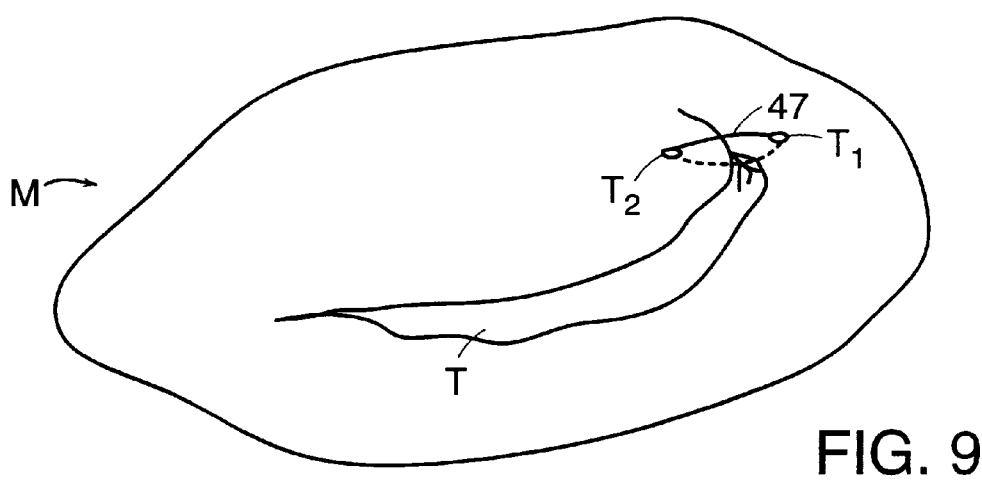
FIG. 9 is the view in FIG. 6 with the suture closed about one portion of the meniscal tear.

FIGS. 6, 7, and 9 provide an isolated view of the needle 14 penetrating the meniscus M as the needle passes through the knee. The cannula 41 and needle driving device 10 have been omitted from the drawings to simplify the portrayal. As illustrated in FIG. 6, the long needle 14 passes through a first target site $T_1$ on the meniscus. The needle passes completely through the meniscus M and exits the knee as shown previously in FIG. 5. FIG. 7 illustrates the needle on its second pass through the meniscus. A second target site $T_2$ adjacent the first site $T_1$ on the meniscus M is selected and penetrated by the needle 14. As shown, the needle 14 is carrying the same suture 47 as that used for the first target site F. The needle 14 passes completely through the meniscus M and out the knee. This forms a loop about the two sides of the meniscus and allows the tear T to be closed when the suture is tied off and pushed down to the site of the tear. FIG. 8 shows that both ends 52 and 53 of the suture 47 are now outside the knee K. A knot is formed with the suture, pushed down to the meniscal tear T, and tied off. As shown in FIG. 9, the tied off suture closes a portion of the tear T in the meniscus. The procedure is repeated until the entire tear T is adequately secured.

Figure 10:
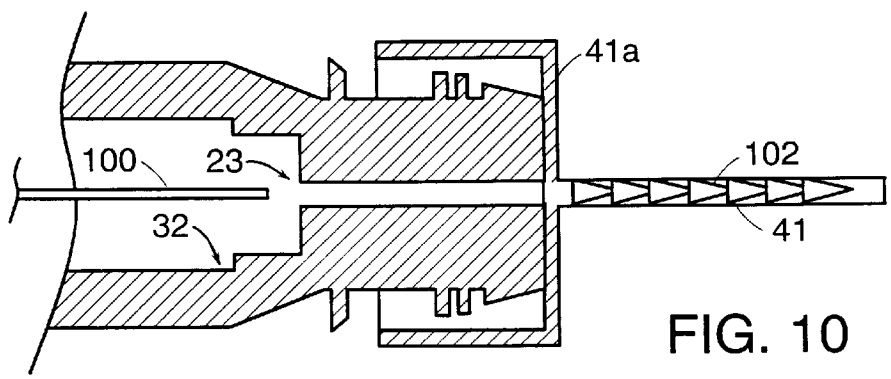
FIG. 10 is a detailed, cross-sectional view of the distal end of a driving assembly and cannula, where the driving assembly includes a cannula for advancing a tissue anchor within the cannula.
Figure 11:
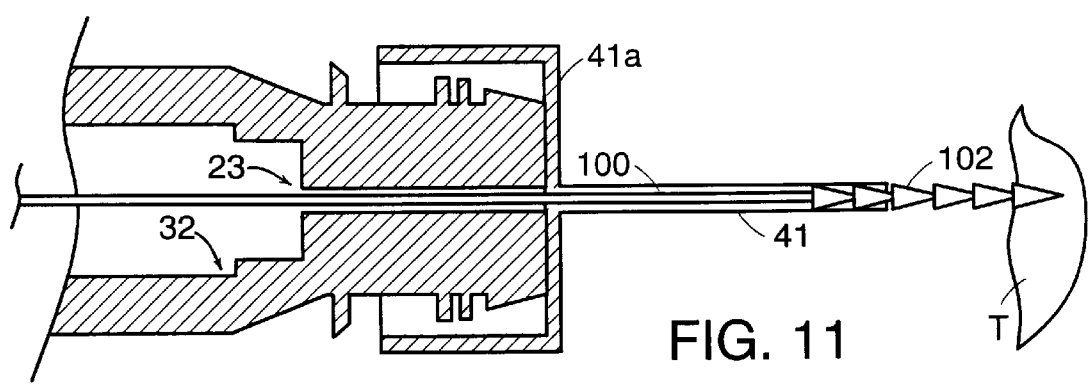
FIG. 11 illustrates the apparatus of FIG. 10 with the obturator advanced for delivering the tissue anchor from a distal end of the cannula into tissue.

Referring now to FIGS. 10 and 11, modification of the apparatus of the present invention for delivering tissue anchors will be described. The apparatus may be identical to that described in FIGS. 1A–1B and FIGS. 2A–2C except that the needle will be replaced with a blunt obturator, and the cannula will be provided with a tissue anchor in its lumen. For convenience, the apparatus of FIGS. 10 and 11 is shown identically to the distal end of the device 40 of FIG. 2A. All identical components have been given identical reference numbers. The cannula 41 is removably attached to the shaft of the driving assembly by luer fitting 41a. An elongate obturator 100 is mounted within the driving assembly and initially disposed proximally of the cannula 41, as shown in FIG. 10. Tissue anchor 102 (which is illustrated as a barbed element, but which may be any self-penetrating and self-anchoring type of anchor), is pre-loaded in the cannula 41. The device is then actuated in a manner similar to the previously described needle drivers, with the obturator 100 advancing into the cannula 41 in order to drive the tissue anchor 102 distally therefrom. The tissue anchor thus enters the target tissue T, typically to seal or reattach torn or otherwise injured tissue.

Figure 12:
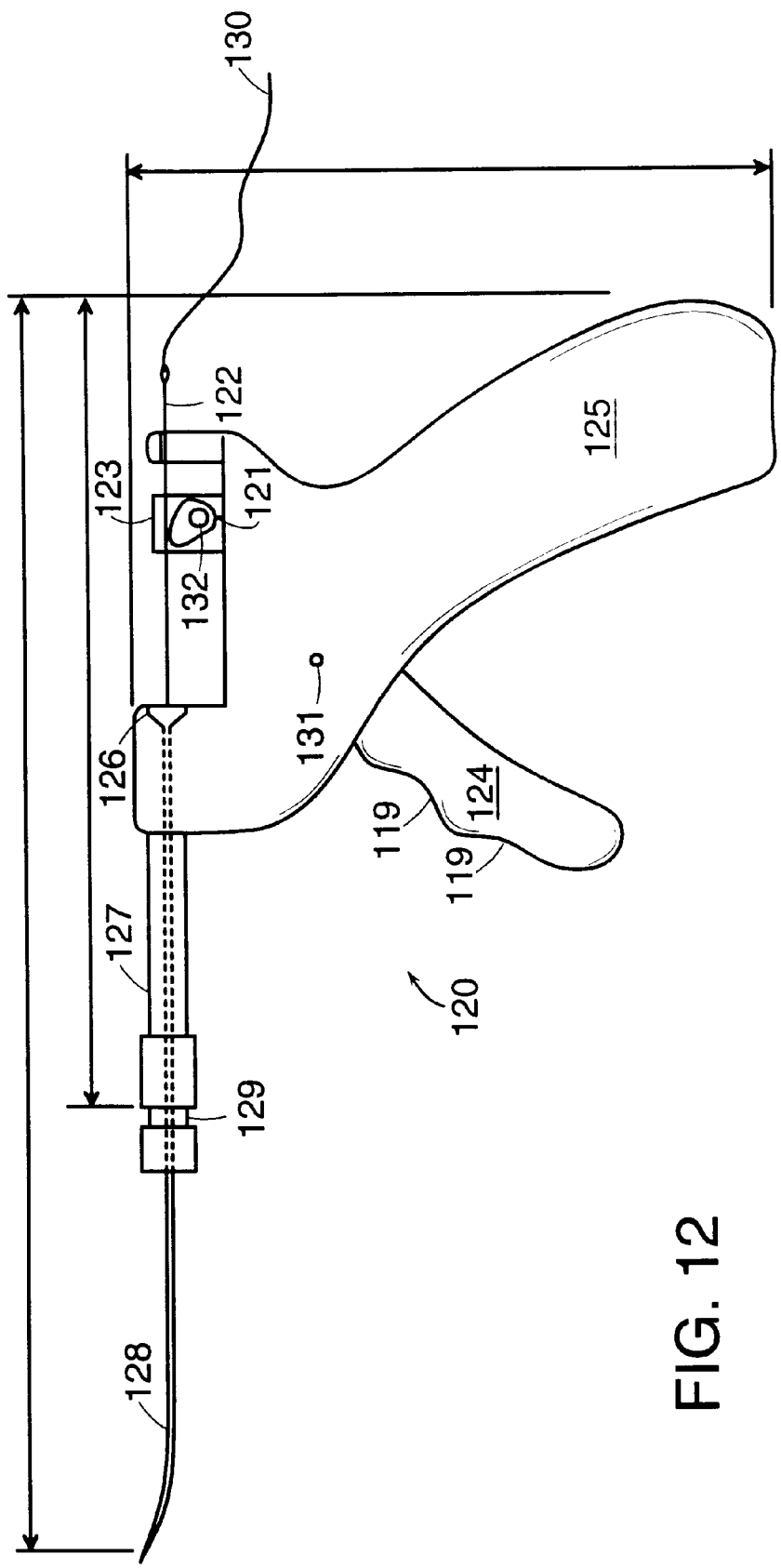
FIG. 12 is a side view of a two-finger pistol grip driver device for delivering surgical or repair material into a joint.

Illustrated in FIG. 12 is a pistol driver 120 with a curved cannula 128 removably connected to driver 120 by a connector hub 129. Pistol driver 120 includes a trigger arm 124 pivotally connected to a handle 125 at pivot point 131. A tube 127, integrally connected to handle 125, includes a funnel-shaped opening 126 at the tube end proximal to the rear of pistol driver 120. Motion of trigger arm 124 activates a cam 121 through a series of internal springs (not shown). Cam 121 is pivotally connected at pivot point 132 to shuttle 123, which is slidably attached to the top of handle 125. When activated, cam 121 cooperates with shuttle 123 to engage and advance a needle 122, carrying a suture 130, into annular tube 127. Funnel-shaped opening 126 of tube 127 helps guide needle 122 into tube 127 as the needle is advanced.

Pistol driver 120 is small and lightweight making it operable by one hand. In use, an operator grips driver 120 in one hand with one or two fingers placed around trigger arm 124 and the remaining fingers wrapped around handle 125. Ridges 119 facilitate gripping of the trigger arm by the operator. Needle 122 is loaded into driver 120 either from the rear or side of the driver and placed between cam 121 and the roof of shuttle 123. Needle 122 is manually advanced into opening 126 and guided into tube 127. Loading needle 122 from the side of driver 120 provides certain advantages over loading from the rear. For instance, needle 122 is usually long in length making it quite unwieldy, which increases the chance that the distal tip of needle 122 will come in contact with the entry area of tube 127 when needle 122 is loaded from the rear. Inadvertent contact with the tube may cause the distal end of needle 122 to be dulled, broken or contaminated. Forceful contact may also cause needle 122 to become warped.

After needle 122 is manually positioned and loaded, the operator depresses trigger arm 124 towards handle 125 which activates the advancement mechanism of cam 121 and shuttle 123 (described in detail below) causing needle 122 to translate either an incremental distance of about 1 mm or a full distance of about 75 mm; the amount of advancement being controlled by the extent to which trigger arm 124 is depressed. The two-finger design of trigger arm 124 provides the operator with more stability and control of pistol driver 120 than one-finger trigger designs.

Needle 122 is advanced through tube 127 and further through cannula 128. The design features of cannula 128 enable easier insertion of needle 122 into a joint. Cannula 128 is rotatable 360 degrees about the axis of tube 127. Once a specific angle is chosen by the operator, cannula 128 is locked into position on hub connector 129.

Figure 13:
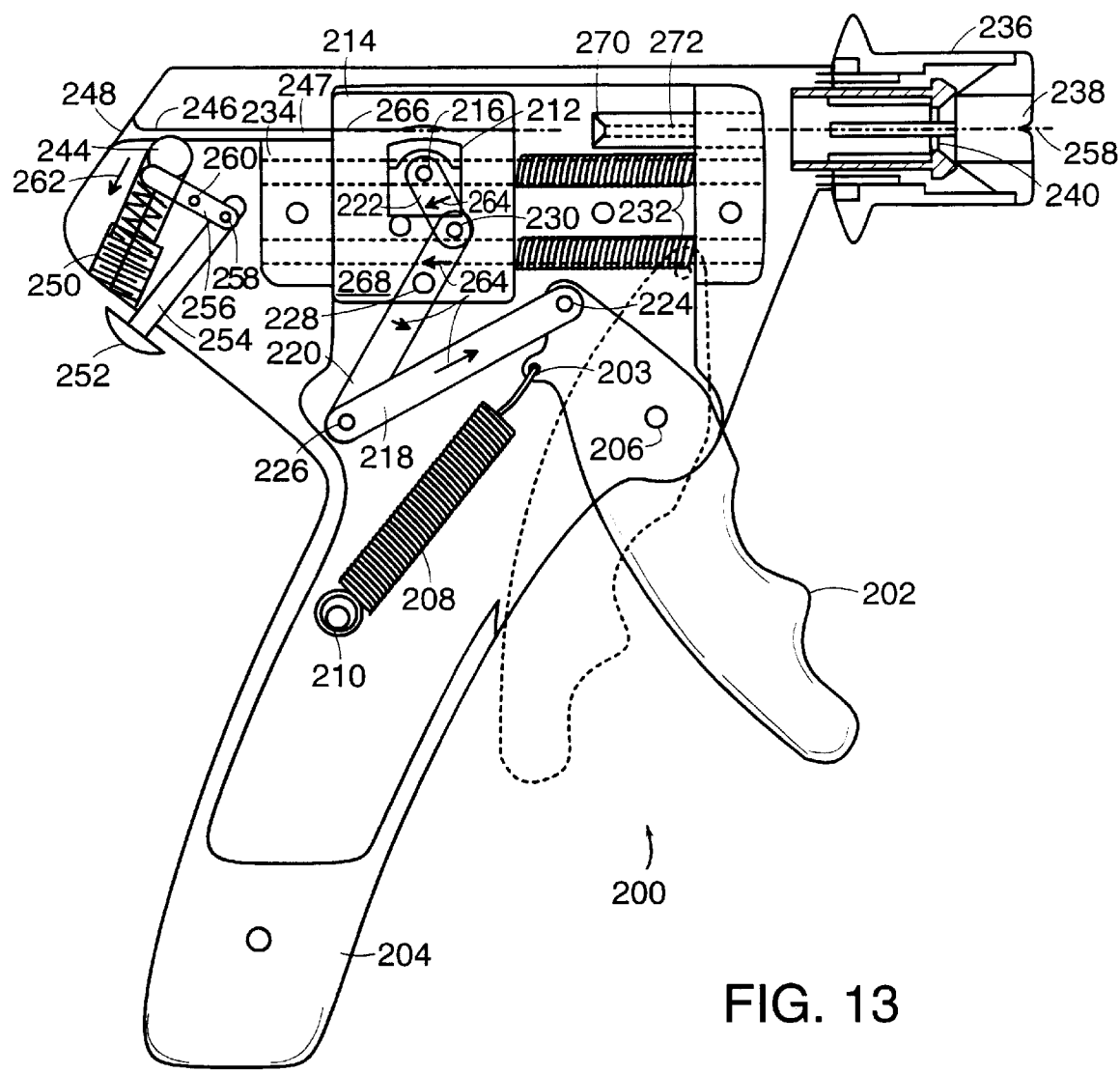
FIG. 13 is a sectional close-up view of the pistol grip driver device of FIG. 12.

Illustrated in FIG. 13, the advancement mechanism and a force-converter device of a pistol driver 200 is shown. The advancement mechanism includes a cam 212 pivotally connected to a shuttle 214 and pivot point 216. The force-converter device includes lever arms 218, 220 and 222 and spring 208. Pistol driver 200 includes a trigger arm 202 pivotally connected to a handle 204 at pivot point 206. Trigger arm 202 includes an end 203 connected to one end of a spring 208 with the other end of the spring attached to handle 204 at attachment point 210. A force applied to trigger arm 202 is transmitted to cam 212 through the series of lever arms 218, 220, 222. One end of lever arm 218 is pivotally connected to trigger arm 202 at pivot point 224, and is pivotally connected at its other end to lever arm 220 at pivot point 226. Lever arm 220 is further pivotally connected to shuttle 214 at pivot point 228 and to lever arm 222 at pivot point 230. Lever arm 222 is fixedly attached to cam 216 such that an incrementally rotating lever arm 222 about pivot point 216 causes cam 212 to incrementally rotate about the same pivot point. Shuttle 214 is slidably attached to handle 204 such that springs 232 urge shuttle 214 against backstop 234.

Cannula 128 (FIG. 12) is connected to pistol driver 200 by inserting the proximal end of the cannula into the distal end 238 of pistol driver 200 while connector hub 236, movably connected to pistol driver 200, is forced toward the cam/shuttle advancement mechanism. Releasing connector hub 236 causes locking mechanism 240 to lock onto the cannula. Locking mechanism 240 can be a system of splines which would enable the cannula to be rotatable 360° about the axis 242 as well as being lockable in one position. Tube 272 extends through pistol driver 200 meeting at one end with the coaxially aligned and attached cannula. Tube 272 includes a funnel-shaped opening 270 at its other end for guiding and directing needle 122 into tube 272.

Pistol driver 200 further includes a needle holding mechanism located at the driver end proximal to the user. The holding mechanism is a rolling cylinder 244 urged to the top 246 of side slot 247 by spring 250. In alternate embodiments, a ball-shaped element can be used in place of rolling cylinder 244. Button 252 is integrally connected to lever arm 254 which is further pivotally connected to lever arm 256 at pivot point 258. Lever arm 256 is pivotally connected to handle 204 at pivot point 260. To release the holding mechanism, button 252 is pressed causing lever arm 256 to rotate about point 260 so that a force is applied in the direction of arrow 262 to spring 250 which causes rolling cylinder 244 to move away from top 246 of inlet 248.

In use, an operator inserts a needle into inlet 248, and manually advances the needle past rolling cylinder 244 and cam 212 until the needle point extends beyond cam 212. Spring 250 urges rolling cylinder 244 against the needle such that rolling cylinder 244 and top 246 of side slot 247 serve as a friction device to hold the needle and to prevent inadvertent backward movement of the needle.

The operator applies a force to trigger arm 202 by squeezing trigger arm 202 towards handle 204 which causes lever arms 218, 220, and 222 to move in respective directions indicated by the arrows 264. When trigger arm 202 is depressed, the above described mechanism is activated enabling incremental advancement of the needle. Since lever arm 222 is fixedly attached to cam 212, movement of the lever arms, in response to the applied force, in the direction of arrows 264 causes cam 212 to rotate and thereby clamp the needle against the roof 266 of shuttle 214. Further squeezing of trigger arm 202 causes shuttle 214 and the needle to translate in the direction of arrow 268 resistively against springs 232. As shuttle 214 slides forward in response to the squeezing of trigger arm 202, funnel-shaped opening 270 of tube 272 captures the needle. The needle is advanced through tube 272 and the cannula and is presented and deployed to the bodily area being surgically repaired. After deployment, the operator reduces the squeezing force applied to trigger arm 202. Consequently, springs 232 urge shuttle 214 back towards backstop 234, and spring 208 urges trigger arm 202 back to its original unsqueezed state. When the needle is released from cam 212, it is in an unengaged condition so that, if desired, it can be manually manipulated.

The system of springs and lever arms described above is able to produce countering forces when desired. For example, the spring mechanism is capable of providing a force greater than that which is provided by the operator such that one gentle squeeze of trigger arm 202 translates into a forceful push of the needle. This enables the operator to penetrate hard tissue or cartilage with the needle with ease. Alternatively, the spring mechanism is able to produce a force less than that provided by the operator. In this case, one squeeze of trigger arm 202 produces a gentle push of the needle thereby enabling the operator to perform delicate puncturing of soft tissue with significantly reduced chance of error which minimizes patient trauma.

Figure 13A:
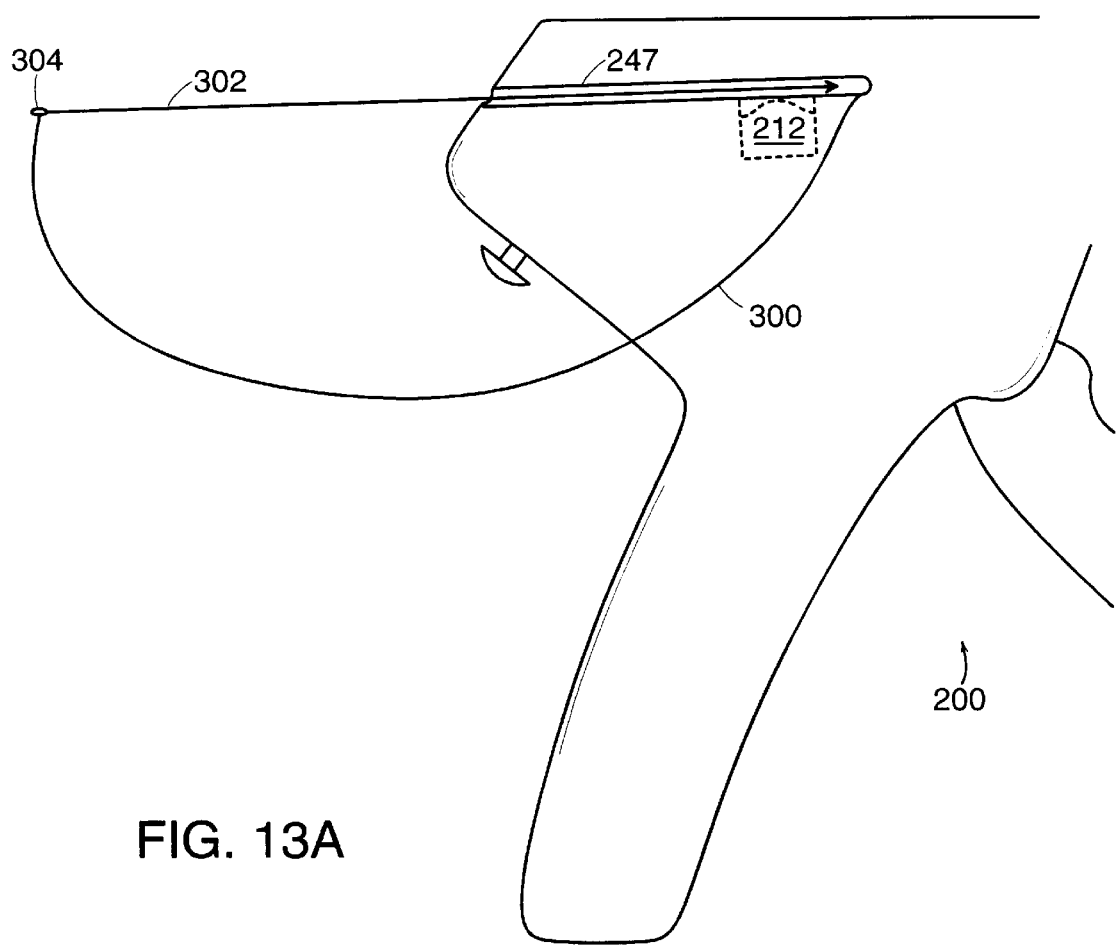
FIG. 13A is a close-up view of the pistol grip driver device of FIG. 12 driving a suture.

Referring to FIG. 13A, an advantageous feature of side slot 247 is illustrated. Suture 300 is connected at one end to needle 302 at point 304. The other end of the suture is connected to another needle that has already been advanced through pistol driver 200. In operation, the first needle is advanced through the device. After pulling the trailing suture 300 out of slot 247, the second needle 302 is placed in position and deployed to the desired bodily location. By moving suture 300 away from slot 247, damage to suture 300 that could be caused by the gripping action of cam 212 is minimized. Furthermore, the potential for damage to the suture by needle 302 is reduced, since the amount of contact between suture 300 and needle 302 is also minimized. After second needle 302 is advanced through driver device 200, the entire suture length is pulled through the device.

In alternate embodiments, pistol driver 120 is used to insert and place other types of insertion material including, but not limited to, soft tissue repair implants, or bone repair implants that may consist of the following material: titanium or stainless or any other metal; biocompatible plastic; suture gut material; cross-linked or expandable collagen or derivatives of collagen. These implants may take the shape of any of the following: a fully or partially threaded screw (either cannulated or noncannulated and headed or headless) with either variable-pitched threads or consistent-pitched threads; a push-in tack (either cannulated or noncannulated); a push-in plug (either cannulated or noncannulated); needles; and suture lengths.

The driver device can be manufactured from stainless steel or from any other commercially available metal (e.g. aluminum or titanium). In other cases, the driver device can be injection molded from medical grade plastic. In some cases, the devise is re-usable and in other cases it may be disposable after a single use. The force-converter device may include torque-inducing wires.

What is claimed is:

1. A driver assembly for implanting surgical device to repair body tissue, the driver assembly comprising:
   a handle having a distal end configured to receive a detachable cannula;
   a trigger arm connected to the handle; and
   an advancement mechanism having a shuttle reciprocatably mounted to said handle and a cam member pivotally connected to the shuttle, said cam member configured to clamp the surgical device against the shuttle in response to a force applied to the trigger arm, said advancement mechanism mechanically coupled to the trigger arm and constructed to receive and incrementally translate the surgical device through the cannula and into the body tissue to be repaired in response to the force applied to the trigger arm.

2. A driver assembly as in claim 1 wherein the handle has a proximal end and the driver assembly includes a return mechanism configured to urge said shuttle towards the proximal end of said handle when said force applied to said trigger arm is released.

3. A driver assembly as in claim 2 wherein said return mechanism includes a spring, positioned between the shuttle and the distal end of the handle to urge the shuttle towards the proximal end of the handle in response to release of the force applied to the trigger arm.

4. A driver assembly as in claim 3 further comprising a force-converter device connected to the trigger arm and to the advancement mechanism, said force-converter device constructed to cause rotation of said cam member and subsequent incremental lineal motion of said shuttle towards the distal end of the handle in response to said force applied to the trigger arm.

5. A driver assembly as in claim 4 wherein the force-converter device includes a spring connected between the trigger arm and the handle.

6. A driver assembly as in claim 5 wherein said force-converter device includes lever arms connected between the trigger arm and the advancement mechanism.

7. A driver assembly as in claim 1 further comprising a cannula having a proximal end removably connected to the distal end of said handle, a distal end, a lumen therethrough, and a length sufficient to extend from the surface of the skin to the surgical sight of the body tissue being repaired.

8. A driver assembly as in claim 7 wherein said handle includes an annular tube having a proximal end, a distal end, and a bore therethrough axially aligned with said lumen, the tube having a funnel-shaped opening at its proximal end, said cannula being removably connected to the distal end of the annular tube.

9. A driver assembly as in claim 1 further comprising a force-converter device connected to the trigger arm and to the advancement mechanism, said force-converter device constructed to cause rotation of said cam member and subsequent incremental lineal motion of said shuttle towards the distal end of the handle in response to said force applied to the trigger arm.

10. A driver assembly as in claim 9 wherein the force-converter device includes a spring connected between the trigger arm and the handle.

11. A driver assembly as in claim 10 wherein said force-converter device includes lever arms connected between the trigger arm and the advancement mechanism.

12. A method for repairing a body tissue tear with a driver assembly having a handle, a trigger arm connected to the handle, a cannula removably connected to a distal end of said handle, and an advancement mechanism mechanically coupled to the trigger arm, said advancement mechanism having a shuttle reciprocatably mounted to said handle and a cam member pivotally connected to the shuttle, the method comprising:
   inserting a first surgical device in the advancement mechanism;
   positioning the cannula of the driver assembly through a skin opening at a first target site adjacent the tissue tear; and
   actuating the advancement mechanism including repeated movement of the trigger arm towards and away from the handle, thereby incrementally advancing the first surgical device through the cannula and the body tissue until at least a portion of the first surgical device passes through a posterior surface of the body tissue.

13. The method of claim 12 wherein the first surgical device has a length of suture connected thereto, and the step of actuating further comprises removing the first surgical device from the body, and disconnecting the length of suture from the first surgical device.

14. The method of claim 13 further comprising:

inserting a second surgical device, having the length of suture connected thereto, in the advancement mechanism;

positioning the cannula of the driver assembly through the skin opening at a second target site adjacent the tissue tear;

actuating the advancement mechanism including repeated movement of the trigger arm towards and away from the handle, thereby incrementally advancing the second surgical device through the cannula and the body tissue tear until at least a portion of the second surgical device passes through the posterior surface of the body tissue;

removing the second surgical device from the body;

disconnecting the length of suture from the second surgical device; and tying the suture.

15. The method of claim 12 wherein said surgical device is a needle having a shaft and a sharpened end.

16. The method of claim 12 wherein said surgical device is an obturator.

17. The method of claim 12 wherein said surgical device is an implant.

18. The method of claim 17 wherein said implant is made of biocompatible, bioresorbable material.

19. The method of claim 18 wherein said biocompatible, bioresorbable material is collagen.

20. The method of claim 18 wherein said biocompatible, bioresorbable material is plastic.

* * * * *